United States Patent [19]
> Sturm et al.

[11] 4,029,787

[45] June 14, 1977

[54] BASICALLY SUBSTITUTED 3-SULFAMOYLBENZOIC ACID DERIVATIVES AND PROCESS FOR THEIR PREPARATION

[75] Inventors: Karl Sturm, Heidesheim; Franz Starey, Frankfurt am Main, both of Germany

[73] Assignee: Hoechst Aktiengesellschaft, Frankfurt am Main, Germany

[22] Filed: Sept. 4, 1975

[21] Appl. No.: 610,388

[30] Foreign Application Priority Data

Sept. 6, 1974   Germany .......................... 2442851

[52] U.S. Cl. .................. 424/248.53; 260/247.1 M
[51] Int. Cl.² ............. C07D 413/02; A61K 31/535
[58] Field of Search ............. 260/268 PH, 247.1 M; 424/248, 248.53

[56] References Cited

OTHER PUBLICATIONS

Arya et al., J. Pharm. Sciences, vol. 58, No. 4, pp. 432–439, (1969).
Das et al., J. of Medicinal Chemistry, vol. 14, No. 9, pp. 890–891, (1971).
Tamayo et al., Chemical Abstracts, vol. 65, p. 13636e, (1966).

*Primary Examiner*—Donald G. Daus
*Assistant Examiner*—Jose Tovar
*Attorney, Agent, or Firm*—Curtis, Morris & Safford

[57] ABSTRACT

Antihypertensively-active 3-sulfamoyl-4-piperazinyl-benzoic acids, optionally substituted in the 2-position by halogen or alkyl, and the esters, amides, and nitriles of these acids are disclosed, as is a method for making these compounds by the reaction of the corresponding 4-halogeno- or 4-alkyl-(or 4-aryl-) sulfonyloxy-benzoic acids (or their esters etc.) with piperazines.

4 Claims, No Drawings

BASICALLY SUBSTITUTED 3-SULFAMOYLBENZOIC ACID DERIVATIVES AND PROCESS FOR THEIR PREPARATION

The present invention relates to basically substituted 3-sulfamoylbenzoic acid derivatives as well as a process for preparing them.

The present invention provides novel basically substituted 3-sulfamoylbenzoic acid derivatives of the general formula I

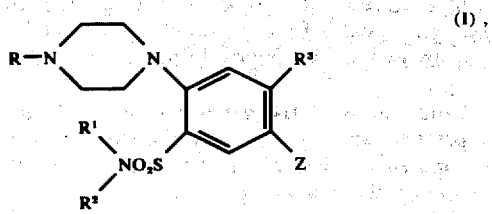

in which R represents a hydrogen atom, an optionally branched and/or mono-unsaturated alkyl radical having from 1 to 6 carbon atoms or a benzyl radical optionally substituted by halogen, such as fluorine, chlorine, bromine, iodine, or by alkyl or alkoxy radicals having from 1 to 4 carbon atoms each, $R^1$ and $R^2$ represent hydrogen atoms, optionally branched unsaturated alkyl, cycloalkyl or cycloalkylalkyl radicals having up to 10 carbon atoms each, which are interrupted by oxygen or sulfur, phenyl or phenylalkyl radicals having from 7 to 10 carbon atoms and being optionally substituted by halogen atoms, alkyl or alkoxy radicals with up to 4 carbon atoms each, the radicals $R^1$ and $R^2$ also possibly being bridged by O, N or S or by a direct C—C bond, thus forming with the sulfonamide nitrogen a 3- to 8-membered heterocycle, $R^3$ represents a hydrogen or a halogen atom or an alkyl radical having from 1 to 4 carbon atoms, and Z stands for a carboxyl group, or a carboxyl group esterified by an aliphatic or araliphatic alcohol having up to 8 carbon atoms, a carbon-amide group which may carry as substituents 1 or 2 aliphatic, araliphatic or aromatic radicals having up to 8 carbon atoms each, which may be interrupted or bridged by O, N or S, or the cyano group.

This invention also provides the salts of these compounds with physiologically tolerable acids and, if a carboxyl group is present, with physiologically tolerable bases.

The present invention also provides a process for the preparation of 3-sulfamoylbenzoic acid derivatives of the formula I, which comprises reacting a compound of the general formula II

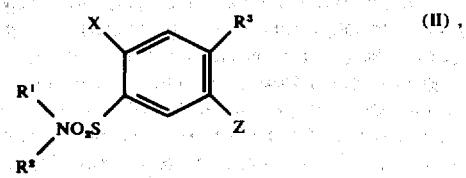

in which X is a halogen atom, such as fluorine, chlorine, bromine, iodine or an alkyl- or arylsulfonyloxy radical, in particular a methane-, ethane-, phenyl- or p-toluene-sulfonyloxy radical, with a piperazine base of the general formula III

in which R, $R^1$, $R^2$, $R^3$ and Z have the meanings specified above in formula I. Subsequently, in the compounds obtained of the general formula I, a cyano group is optionally hydrolyzed to give the carbonamide or carboxyl group, a carboxyl group is esterified or amidated in usual manner, an unsubstituted carbonamide group is converted into the cyano group, benzyl radicals bound by way of N or O atoms are split off by catalytic hydrogenation, or, if at least one of the radicals R, $R^1$ and $R^2$ represents a hydrogen atom, the compounds are alkylated, alkenylated or aralkylated in the usual manner at the piperazine nitrogen and/or at the sulfonamide group, or, if at least one of the radicals R, $R^1$ and $R^2$ represents an unsubstituted aliphatic radical, double bonds are hydrogenated. Subsequently, the products of the invention may be converted into their salts with physiologically tolerable acids; those products of the invention which have a free carboxyl group may be converted accordingly with physiologically tolerable bases into salts, particularly the alkali metal salts, the alkaline earth metal salts or ammonium salts.

The radicals R, $R^1$, $R^2$ and $R^3$ may represent, for example, the methyl or ethyl radical, the radicals R, $R^1$ and $R^2$ may also stand for an allyl or benzyl radical or one of the isomeric propyl, butyl, pentyl or hexyl radicals. Furthermore, $R^1$ and $R^2$ represent, for example, a 2-methoxyethyl, 2-methylmercaptoethyl, 2-ethoxyethyl, 2-ethylmercaptoethyl, 3-methoxypropyl, cyclopentyl, cyclohexyl, cyclohexenyl, cycloheptyl, cyclooctyl, cyclopentylmethyl, or tetrahydrofurfuryl radical, the phenyl, benzyl radical or one of the isomeric phenylethyl or phenylpropyl radicals, the phenyl radical optionally carrying as substituents one or several chlorine atoms, methyl or methoxy groups, or $R^1$ and $R^2$ may stand for the piperonyl, the cinnamyl or the phenoxyethyl radical. Moreover the group

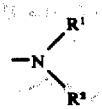

may represent, for example, a pyrrolidino, piperidino, hexamethylene-imino, morpholino, thiomorpholino, isoindolino, N-phenyl-piperazino, or 4-phenyl-piperidino radical.

As esters of the carboxylic acids of the general formula I there are mentioned, for example, the methyl or ethyl ester, the isomeric propyl and butyl esters, as well as the allyl and benzyl ester. Suitable amides, besides the unsubstituted amide, are for example the methylamide, dimethylamide, ethylamide, diethylamide, the isomeric propyl, dipropyl, butyl and dibutyl amides, the allylamide, cyclopentyl-, cyclohexyl-, N-methylcyclohexyl-, cycloheptyl-, cyclohexylmethyl-, N-methylcyclohexylmethyl-, tetrahydrofurfuryl-, N-methyltetrahydrofurfuryl-, and 2-ethoxyethylamides, the anilide, N-methylanilide, N-ethylanilide, N-benzylanilide, benzylamide, N-methylbenzylamide, dibenzylamide, diphenylamide, as well as the derivatives thereof which have been substituted in the phenyl radical by chlorine atoms, methyl or methoxy groups, the furfurylamide, N-methylfurfurylamide, the isomeric pyridylmethylamides and N-methyl-pyridyl-methylamides, the pyrrolidide, piperidide, morpholide, thiomorpholide, as well as the N-methyl-, N-benzyl- and N-phenylpiperazide.

The starting products of the general formula II are partly known. They can be prepared by reacting carboxylic acids of the general formula IV, in which X is defined as in formula II, at a temperature in the range of from 60° to 150° C, with excess chlorosulfonic acid, isolating the sulfochloride formed by introducing the cooled reaction soluton into ice and reacting the said sulfochloride with ammonia or an amine of the general formula

to give compounds of the general formula V

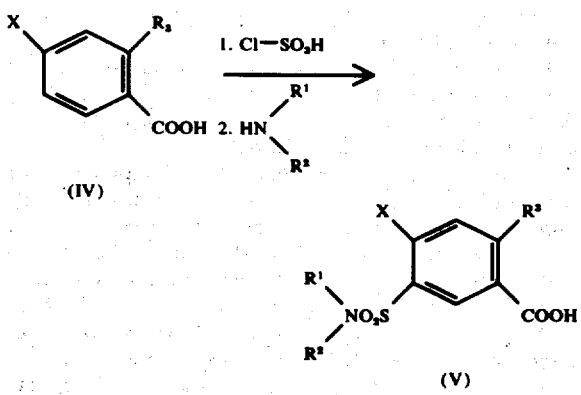

The carboxylic acids of the general formula V can be advantageously converted, via the acid chloride as intermediate product prepared by using thionylchloride, into the corresponding esters, amides or nitriles of the general formula II.

There are also novel starting products which correspond to the general formula IIa

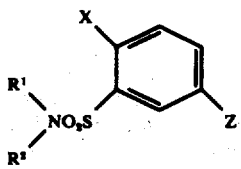

in which X, Z, $R^1$ and $R^2$ are defined as in the general formula I, with the restriction that $R^2$ may not represent a hydrogen atom or a $C_{1-3}$ alkyl radical.

In accordance with the process claimed, the compounds of the general formula II are reacted with a piperazine derivative of the general formula III, in which process the radical X is substituted by the corresponding piperazine radical in nucleophilic manner. As starting products, use is advantageously made, in general of those compounds in which X represents a chlorine atom. They react, if Z is a carboxyl group, with the respective piperazine derivatives at a temperature of from 130° to 150° C. If Z represents an ester or amide group, the reaction temperature is reduced by about 20° C. If the radical Z stands for a cyano group, the chlorine atom is in particular strongly activated, so that the reaction temperature, with respect to the corresponding carboxylic acid, is lower by about 40° C.

Those compounds of the general formula II, wherein X stands for a bromine or iodine atom, are less reactive than the corresponding chlorine compounds, whereas the corresponding fluorine derivatives react much more easily.

Such fluorine derivatives are advantageously used as starting products, if $R^3$ represents a chlorine, bromine or iodine atom, as only the fluorine atom reacts in a wide range of temperature. It is advantageous to choose for the selective fluorine exchange reaction temperatures of from 70° to 110° C, the lower limit being applicable for compounds with Z = CN, whereas the upper limit is applicable for compounds with Z = COOH.

Compounds of the general formula II, in which X represents an alkyl-or aryl-sulfonyloxy radical, can be compared in view of their reactivity with the corresponding chlorine compounds.

If, in the starting compounds of the general formula II, the substituents X and $R^3$ are identical and thus represent the same halogen atom, i.e. if for example the 2,4-dichloro- or 2,4-dibromo-benzoic acid derivatives of the general formula II are used, the reaction develops in the desired manner only if the radical Z represents the cyano group, since the latter compound preferably activates the halogen atom in the p-position. The optimum reaction temperature is in this case in the range of from 100° to 120° C.

The reaction may be carried out without a solvent, the piperazine component being used advantageously in an excess amount in order to keep the reaction mixture in the liquid state. However, the reaction is advantageously carried out while adding a chemically inert diluent that can be mixed with water, such as for example dimethylformamide, dimethylacetamide, diethyleneglycol-dimethylether, glycoldiethylether, dioxane, ethanol or isopropanol. In theory, one molar equivalent of the piperazine component is in this case sufficient, since the second nitrogen atom binds the acid HX set free. However, the reaction is considerably accelerated if from 1.5 to 3.0 molar equivalents of the base are used.

In order to work up the reacton mixture, it is advantageously poured into water. If the final product is to be isolated in its free form, the pH value of the mixture subsequently adjusted with sodium hydroxide solution and/or hydrochloric acid at 8.0 to 8.5, if the radical Z represents a carboxyl group; the pH is adjusted at 9.5 to 10.5, if the radical Z represents a carboxylic acid ester, a carbonamido or a cyano group. As a rule, the products of the invention are obtained in a crystalline from either immediately or after being allowed to stand over night at room temperature. Amorphous reaction products are advantageously separated by shaking with acetic ester, methylene chloride or chloroform. In order to recrystallize the crude products, use may be made for example of methanol, ethanol, isopropanol, acetic ester, butyl acetate, dioxane, nitromethane, or mixtures of solvents, such as ethanol/water, dioxane/water, diethylformamide/ water, acetic ester/diisopropylether or acetic ester/petroleum ether.

In many cases it is advantageous to isolate the final products as salts of physiologically tolerable acids. In this case, the reaction solution is introduced into a diluted aqueous solution of the acid corresponding to the radical X in the starting product, for example 1N hydrochloric acid. These acid addition salts of the products of the invention are hardly soluble in water and are thus separated almost completely, even in the case where the acid was used in a multifold molar excess. Under these conditions the salt formation takes place only at the nitrogen atom of the piperazine ring which has not been substituted by an aromatic radical. In order to recrystallize the acid addition salts with a molar equivalent of HX, use is advantageously made of water, methanol, ethanol, dioxane, dimethylformamide, and mixtures of these solvents. To prepare other acid addition salts, the bases of the general formula I are dissolved and recrystallized from one of the above-mentioned solvents while adding an equivalent amount of the corresponding acid.

Those products of the invention which have a free carboxyl group are converted, for example, into the correspondng alkali metal, alkaline earth metal or ammonium salts by adding physiologically tolerable bases.

If the primary products of the invention which have a free carboxyl group are to be converted subsequently into the corresponding carboxylic acid esters, carbonamides or nitriles, they are first advantageously converted into the carboxylic acid chloride hydrochlorides, for example by heating with excess thionyl chloride, and are then reacted in the usual manner with the respective alcohols, amines or ammonia. Carbamoyl compounds can be converted into the corresponding nitriles, for example by heating with excess phosphorus oxychloride at a temperature in the range of from 70° to 100° C.

The conversion of esters, amides or nitriles of the general formula I into the corresponding carboxylic acids is performed advantageously by means of diluted sodium hydroxide solution or potassium hydroxide solution, and the partial hydrolysis of a nitrile to give an amide is advantageously carried out by means of diluted hydrochloric or sulfuric acid under reflux.

The subsequent hydrogenation of olefinic double bonds in the radicals R, $R^1$ and $R^2$ of the products of the invention is advantageously carried out by catalytic hydrogenation in the presence of Raney - Nickel at an elevated presssure. If benzyl radicals bound by an oxygen or nitrogen atom are to be eliminated later on, the hydrogenation is advantageously carried out in the presence of palladium black in a shaking flask. Under these conditions, benzyl radicals bound to the nitrogen atom of the sulfonamide group remain unchanged. Suitable solvents for these hydrogenation reactions are, for example, methanol, ethanol, tetrahydrofurane and dioxane.

If one or several radicals R, $R^1$ or $R^2$ are to be introduced subsequently into compounds of the general formula I, they are reacted in the usual manner, and optionally stepwise, with the halides or sulfonic acid esters corresponding to these radicals, such as benzyl bromide, allylbromide, ethyl iodine, or dimethyl sulfate.

Besides the products of the invention mentioned in the Examples, the following compounds, for example, may be prepared according to the process of the invention:

3-Dimethylsulfamoyl-4-(4-methylpiperazine-1-yl)-benzoic acid-methylamide, -dimethylamide, -diethylamide, -n-propylamide, -isobutylamide, -2-ethoxyethylamide, -allylamide, -benzylamide, -N-methylbenzylamide, -furfurylamide, -N-methylfurfurylamide, -tetrahydrofurfurylamide, -N-methyltetrahydrofurfurylamide, -pyrrolidide, -piperidide, -morpholide, -cyclohexylamide, -N-methyl- cyclohexylamide, -cyclohexylmethylamide, -2-pyridylmethylamide,- 3-pyridylmethylamide, -N-methyl-4-pyridylmethylamide, -anilide, -2-chloroanilide, -m-toluidide, 4-methoxyanilide, -N-methyl-4-chloroanilide, -2-phenylethylamide, -piperonylamide, -ethylester, -isopropylester, -n-propylester and -isobutylester; 3-diethylsulfamoyl-4-(4-methylpiperazine-1-yl)-benzoic acid-nitrile, -amide, -methylamide, -dimethylamide, -ethylamide, -diethylamide, -n-propylamide, -isopropylamide, -n-butylamide, -isobutylamide, -2-ethoxyethylamide, -allylamide, -benzylamide, -N-methylbenzylamide, -tetrahydrofurfurylamide, -N-methylfurfurylamide, -pyrrolidide, - piperidide, -morpholide, -N-phenylpiperazide, -cyclohexylamide, -N-methylcyclohexylamide, -3-pyridylmethylamide, -dibenzylamide, -anilide, -N-methylanilide, -3-chloroanilide,-p-toluidide, -2-methoxyanilide, -N-methyl-4-methoxyanilide, -methylester, -ethylester, -isopropylester, -n-butylester, -benzylester and -3-pyridylmethylester; 4-(4-methylpiperazine-1-yl)-3-pyrrolidinosulfonylbenzoic acid, 4-(4-methylpiperazine-1-yl)-3-pyrrolidinosulfonylbenzoic acid-nitrile, -amide, -methylamide, -dimethylamide, -ethylamide, -diethylamide, -n-propylamide, -isopropylamide, -n-butylamide, -isobutylamide, -2-methoxyethylamide, -2-ethoxyethylamie, -2-ethylmercaptoethylamide, -allylamide, -benzylamide, -N-methyl-benzylamide, -tetrahydrofurfurylamide, -pyrrolidide, -piperidide, -morpholide, -thiomorpholide, -N-phenylpiperazide, -N-methylpiperazide, -cyclohexylamide, -N-methylcyclohexylamide, -cyclohexylmethylamide, -4-pyridylmethylamide, -dibenzylamide, -anilide, -N-methylanilide, 2-chloroanilide, -m-toluidide, -3-methoxyanilide, -N-methyl-2-methoxyanilide, -4-chloro- 2-methoxy-anilide, -methylester, -ethylester, -isopropylester, -n-butylester;

4-(4-methylpiperazine-1-yl)-3-mmorpholinosulfonyl-benzoic acid-nitrile, -amide, -methylamide, -dimethylamide, -ethylamide, -diethylamide, -n-propylamide, -isobutylamide, -allylamide, -pyrrolidide, -piperidide, -morpholide, -cyclohexylamide, -N-methyl-cyclohexylamide, -benzylamide, -N-methylbenzylamide, -tetrahydrofurfurylamide, -N-methyltetrahydrofurfurylamide, -N-phenylpiperazide, -furfurylamide, -N-methylfurfurylamide, -4-pyridylmethylamide, -N-methyl-4-pyridylmethylamide, -anilide, -N-methylanilide, -methylester, -ethylester and -benzylester;

4-(4-methylpiperazine-1-yl)-3-sulfamoylbenzoic acid-methylamide, -dimethylamide, -ethylamide, -diethylamide, -n-propylamide, -di-n-propylamide, -n-butylamide, -isobutylamide, -allylamide, -pyrrolidide, -piperidide, -2-ethoxyethylamide, -N-methyl-2-ethoxyethylamide, -N-methyl-3-methoxypropylamide, -2-ethylmercaptoethylamide, -2-hydroxyethylamide, -N-methyl- 2-hydroxyethylamide, -tetrahydrofurfurylamide, -N-methyltetrahydrofurfurylamide, -furfurylamide, -2-pyridylmethylamide, -3-pyridylmethylamide, -4-pyridylmethylamide, -N-methyl-2-pyridylmethylamide, -N-methyl-3-pyridylmethylamide, -N-methyl-4-pyridylmethylamide, -cyclohexylamide, -N-methylcyclohexylamide, -piperonylamide, -anilide, -N-methylanilide, -N-ethylanilide, -2-chloroanilide, -4-methoxyanilide, -dibenzylamide, -2-thienylmethylamide, -methylester, -isopropylester, -n-butylester and -benzylester; 4-(4-methylpiperazine-1yl)-3-methylsulfamoylbenzoic acidamide, -nitrile, -ethylester, -morpholide, -N-methylfurfurylamide, -methylamide, -dimethylamide, -ethylamide, -diethylamide, -n-propylamide, -di-n-propylamide, -n-butylamide, -isobutylamide, -allylamide, -pyrrolidide, -piperidide, -2-ethoxyethylamide, -N-methyl-2-ethoxyethylamide, -N-methyl-3-methoxypropylamide, -2-ethylmercaptoethylamide, -2-hyroxyethylamide, -N-methyl-2-hydroxyethylamide, -tetrahydrofurfurylamide, -N-methyltetrahydrofurfurylamide, -furfurylamide, -2-pyridylmethylamide, -3-pyridylmethylamide, 4-pyridylmethylamide, -N-methyl-2-pyridylmethylamide, -N-methyl-3-pyridylmethylamide, -N-methyl-4-pryridylmethylamide, -cyclohexylamide, -N-methyl-cyclohexylamide, -benzylamide, -N-methylbenzylamide, -piperonylamide, -anilide, -N-methylanilide, -N-ethylanilide, -2-chloroanilide, -4-methoxyanilide, -dibenzylamide, -2-thienylmethylamide, -methylester, -isopropylester, -n-butylester and -benzylester;

3-ethylsulfamoyl-4-(4-methylpiperazine-1-yl)-benzoic acid-nitrile, -amide, -morpholide, -N-methylfurfurylamide, -ethylester, -methylamide, -dimethylamide, -ethylamide, -diethylamide, -n-propylamide, -di-n-propylamide, -n-butylamide,-isobutylamide, -allylamide, -pyrrolidide, -piperidide, -2-ethoxyethylamide, -N-methyl-2-ethoxyethylamide, -N-methyl-3-methoxypropylamide, -2-ethylmercaptoethylamide, -2-hydroxyethylamide, -N-methyl-2-hydroxyethylamide, -tetrahydrofurfurylamide, -N-methyltetrahydrofurfruylamide, -furfurylamide, -2-pyridylmethylamide, -3-pyridylmethylamide, -4-pyridylmethylamide, -N-methyl-2-pyri dylmethylamide, -N-methyl-3-pyridylmethylamide, -N-methyl-4-pyridylmethylamide, -cyclohexylamide, -N-methyl-cyclohexylamide, -benzylamide, -N-methylbenzylamide, -piperonylamide, -anilide, -N-methylanilide, -N-ethylanilide, -2-chloroanilide, -4-methoxyanilide, -dibenzylamide, -2-thienylmethylamide, -methylester, -isopropylester, -n-butylester and -benzylester; 4-(4-methylpiperazine-1-yl)-3-piperidinosulfonylbenzoic acid, 4-)4-methylpiperazine-1-yl)-3-piperidonosulfonylbenzoic acidamide, -nitrile, -morpholide, -N-methylfurfurylamide, -ethylester, -methylamide, -dimethylamide, -n-porpylamixde, -di-n-propylamide, -n-butylamide, -isobutylamide, -allylamide, -pyrrolidide, -piperidide, -2-ethoxyethylamide, -N-methyl-2-ethoxyethylamide, ;N-methyl-3-methoxypropylamide, -2-ethylmercaptoethylamide, 2-hydroxyethylamide, -N-methyl-2-hyddroxyethylamide, -tetrahydrofurfruylamide, -N-methyltetrahydrofurfruylamide, -furfurylamide, -2-pyridylmethylamide, -3-pyridylmethylamide, -4-pyridylmethylamide, -N-methyl- 2-pyridylmethylamide, -N-methyl-3-pyridylmethylamide, -N-methyl- 4-pyridylmethylamide, -cyclohexylamide, -N-methyl-cyclohexylaide, -benzylamide, -N-methylbenzylamide, -piperonylamide, -anilide, -N-methylanilide, -N-ethylanilide, -2-chloroanilide, 4-methoxyanilide, -dibenzylamide, -2-thienylmmethylamide, -methylester, -isopropylester, -n-butylester and -benzylster; 6-chloro-4-(4-methul-piperazine-1-yl)-3-morpholinosulfonylbenzoic acid, 6-chloro-4-(4-methylpiperazine-1-yl)-3-dimethylsulfamoylbenzoic acid, 6-chloro-4-(4-methulpiperazine-1-yl)-3-sulfamoylbenzoic acidbezylamide, -N-methylbenzylamide, -furfurylamide, -N-methylfurfurylamide, -dimethylamide and -morpholide.

Salts of the compounds according to the invention suitable for therapeutical use are preferably acid addition salts, such as the monohydrochloride, the neutral or acid sulfate, the primary, secondary or tertiary phosphate, the methane or p-toluene sulfate, or the salt of an organic acid, for example, the maleate or citrate. However, for special purposes alkali metal salts, preferably the monosodium salt or the monopotassium salt may also be used.

As established by animal test carried out on rats and dogs, the compounds of the invention have hypotensive properties that are valuable for therapeutical use.

Because the therapeutic index is very high and because no undesired side effects have been observed, the compounds of the invention are excellent agents for the treatment of high blood pressure, especially of essential hypertonia in human patients.

The preparations are preferably offered in unit dosage form, for example as a tablet, dragee, capsule or suppository. They may contain, per unit dose, from 10 to 500 mg of the active substance, either in the free form or in the form of the above-mentioned acid addition or alkali metal salts, the content of carrier substances possibly being up to 90% of the preparation.

For intravenous administration, there is preferably used an aqueous solution of an acid addition salt of a compound of the invention, which solution may optionally contain an additional solubilizer, in the form of ampules having a content of from 2 to 50 mg of the respective active substance.

Any preparation of the invention may contain other therapeutically active components suitable for the treatment of high blood pressure, for example, saluretics.

The following Examples serve to illustrate the invention.

EXAMPLE 1

4-(4-Methylpiperazine-1-yl)-3-sulfamoyl-benzoic acid a. A mixture consisting of 118 g of 4-chloro-3-sulfamoylbenzoic acid (0.5 mole) and 150 ml of N-methylpiperazine was heated, while stirring, for 6 hours at a temperature of from 140° to 145° C. Subsequently the reaction solution was poured into 1.0 of water and was neutralized with 5N HCl. After standing for 1 hour at room temperature, the crystalline precipitate suction-filtered and was recrystallized from water, while activated charcoal was added.

Yield: 68 g (45% of the theory), degradation point: 315° C.

b. 280 Grams of 4-(4-methylpiperazine-1-yl)-3-sulfamoylbenzonitrile were heated under reflux together with 3 l of 2N NaOH for 3 hours. After the clear reaction solution had cooled to room temperature, it was neutralized with 5N HCl. The carboxylic acid which had precipitated in a crystalline form and had been allowed to stand for a short time at room temperature suction-filtered, was washed with water and dried on a steam bath.

Yield: 268 g (89% of the theory), degradation point: 315° C.

EXAMPLE 2

6-Chloro-4-(4-methylpiperazine-1-yl)-3-sulfamoylbenzoic acid

A mixture consisting of 50 g of 4,6-dichloro-3-sulfamoylbenzonitrile (0.2 mole), 100 ml of dioxane and 22 g of N-methylpiperazine (0.22 mole) was heated, while stirring, for 4 hours at 100° C. Subsequently the reaction solution was poured into 0.4 l of water, and the pH value was adjusted to 8.0 by means of 2N NaOH. The 6-chloro-4-(4-methylpiperazine-1-yl)-3- sulfamoylbenzonitrile which had separated in a crystalline form was dissolved and recrystallized from ethanol.

Yield: 43 g (68% of the theory, melting point: 227° to 228° C.

For hydrolysis, the nitrile obtained was heated with 0.3 l of 2N NaOH and 0.3 l of dioxane for 2 hours under reflux. Subsequently the reaction solution was evaporated in vacuo. The residue was mixed with 0.5 l of water and was neutralized with 2N HCl. The crystalline precipitate was suction-filtered, washed with water and dried on a steam bath.

Yield: 33 g (65% of the theory), melting point: above 330° C.

EXAMPLE 3

6-Methyl-4-(4-methylpiperazine-1-yl)-3-sulfamoylbenzoic acid-hydrochloride 125 g of 4-chloro-6-methyl-3-sulfamoylbenzoic acid (0.5 mole) were heated under reflux with 0.5 l of N-methylpiperazine for 6 hours. Subsequently the excess base was eliminated in vacuo, and the residue was dissolved in 1 l of water. After the solution had been acidified with concentrated hydrochloric acid, the final product precipitated in a crystalline form. After having stood at room temperature for 1 hour, it was suction-filtered and was dissolved and recrystallized from 50% ethanol, while activated charcoal was added.

Yield: 102 g (58% of the theory), degradation point: 302° C.

EXAMPLE 4

4-(4-Methylpiperazine-1-yl)-3-methylsulfamoylbenzoic acid-hydrochloride

250 Grams of 4-chloro-3-methylsulfamoylbenzoic acid (1.0 mole) were stirred with 0.3 l of N-methylpiperazine for 4 hours at 130° C. When the hot reaction solution was introduced into 2 l of 2N HCl, the final product precipitated immediately in a crystalline form. The crude product was purified by recrystallization from a 2:2:1 mixture of ethanol/water/dimethylformamide.

Yield: 155 g(45% of the theory), melting point: 328° C.

EXAMPLE 5

3-Dimethylsulfamoyl-4-(4-methylpiperazine-1-yl)-benzoic acid-hydrochloride

The reaction was carried out in accordance with Example 4, while using 264 g of 4-chloro-3-dimethylsulfamoylbenzoic acid (1.0 mole) as starting material. The crude hydrochloride obtained was recrystallized from 50% ethanol.

Yield: 230 g (63% of the theory), melting point: 269° to 271° C.

The same compound was obtained if 3-dimethylsulfamoyl-4-(4-methylpiperazine-1-yl)-benzoic acid-benzylester-hydrochloride, prepared according to Example 18 and dissolved in 90% tetrahydrofurane, was hydrogenated in the presence of palladium black. The solution separated from the catalyst was subsequently evaporated, and the residue was recrystallized from 50% ethanol.

Yield: 92% of the theory.

EXAMPLE 6

4-(4-n-butylpiperazine-1-yl)-6-chloro-3-sulfamoylbenzoic acid

126 Grams of 6-chloro-4-fluoro-3-sulfamoylbenzoic acid (0.5 mole) were stirred with 0.2 l of N-butylpiperazine for 2 hours at 110° C. Subsequently the reaction solution was poured into 2 l of water, a small amount of amorphous precipitate formed was separated, and the filtrate was adjusted to a pH of 7.5 with 2N HCl. After having stood overnight at room temperature, the crystalline precipitate was suction-filtered and was recrystallized from a mixture of ethanol and water.

Yield: 41 g (22% of the theory), degradation point: 295° to 296° C.

EXAMPLE 7

4-(4-Methylpiperazine-1-yl)-3-sulfamoylbenzoic acid-N-methyl-2-furylmethylamide

103 Grams of 4-chloro-3-sulfamoylbenzoic acid-N-methyl-2-furylmethylamide (0.3 mole) were heated under reflux with 0.3 l of N-methylpiperazine for 5 hours. After the reaction solution had been poured into 2 l of water, the pH value of the mixture was adjusted to 8.0 with 5N HCl. After standing at room temperature for 3 days, the separated yellow resin had crystallized. The reaction product was suction-filtered, washed thoroughly with water and was recrystallized from a mixture of methanol and water.

Yield: 53 g (45% of the theory), melting point: 125° C.

EXAMPLE 8

4-(4-Methylpiperazine-1-yl)-3-sulfamoylbenzoic acid-ethylester

141 Grams of 4-chloro-3-sulfamoylbenzoic acid-ethylester (0.5 mole) were stirred for 1 hour at 110° C with 250 ml of N-methylpiperazine. The crystalline precipitate obtained after the reaction solution had been poured into 2.0 l of water suction-filtered, was washed with water, dried on the steam bath and recrystallized twice from a mixture of diisopropylether and acetic ester.

Yield: 79 g (48% of the theory), melting point: 148° to 149° C.

EXAMPLE 9

4-(4-Methylpiperazine-1-yl)-3-phenylsulfamoyl-benzoic acid

156 Grams of 4-chloro-3-phenylsulfamoyl-benzoic acid (0.5 mole) were stirred with 0.3 l of N-methylpiperazine for 4 hours at 130° C. Subsequently the reaction solution was introduced, while stirring, into 2.0 l of water and the pH was adjusted to 7 by means of glacial acetic acid.

From the solution, which was clear at first, the final product precipitated in a crystalline form after having stood overnight at room temperature. In order to remove secondary products, the crude product was boiled with ethanol for a short time and was suction-filtered while still hot.

Yield: 145 g (77% of the theory), melting point: 252° to 253° C.

EXAMPLE 10

3-(N-Methyl-benzylaminosulfonyl)-4-(4-methylpiperazine-1-yl)-benzoic acid

The reaction was carried out in a manner analogous to that of Example 9, using 170 g of 4-chloro-3-(N-methylbenzylaminosulfonyl)-benzoic acid (0.5 mole) as the starting material.

Yield: 89 g (44% of the theory), melting point: 232° to 233° C.

EXAMPLE 11

4-(4-Methylpiperazine-1-yl)-3-sulfamoylbenzoic acid-amide

165 Grams of 4-chloro-3-sulfamoylbenzoic acid-amide (0.7 mole) were stirred with 0.3 l of N-methylpiperazine for 1 hour at 130° C. Subsequently the reaction mixture was diluted with 2 l of water, and the crystalline precipitate was suction-filtered. The crude product (150 g with a degradation point of 301° C) was dissolved in 3 l of 0.5N HCl and, after the solution had been decolorized with activated charcoal, the said product was precipitated in a crystalline state, at pH 8, by means of 2N ammonia.

Yield: 132 g (63% of the theory), degradation point: 305° C.

EXAMPLE 12

4-(4-Methylpiperazine-1-yl)-3-morpholinosulfonylbenzoic acid

273 Grams of 4-chloro-3-morpholinosulfonylbenzoic acid (1.0 mole) were heated under reflux for 5 hours with 0.5 l of N-methylpiperazine. Subsequently the excess base was completely eliminated in vacuo, the residue was dissolved in 2 l of water, an the pH value of the solution was adjusted to 8 by means of 5N HCl. After standing for 3 days at room temperature, the crystalline precipitate was suction-filtered and was recrystallized from water.

Yield: 150 g (40% of the theory), melting point: 274° to 275° C.

EXAMPLE 13

4-(4-Methylpiperazine-1-yl)-3-sulfamoylbenzoic acid-morpholidehydrochloride

183 Grams of 4-chloro-3-sulfamoylbenzoic acid-morpholide (0.6 mole) were stirred with 0.3 l of N-methylpiperazine for 3 hours at 130° C. Subsequently the excess base was eliminated in vacuo, the residue was dissolved in 0.5 l of water, and the pH of the solution was adjusted to 7 by means of 5N HCl. After having stood in the refrigerator for several days, the reaction product which had separated in a crystalline form was suction-filtered and was recrystallized from ethanol of 90% strength.

Yield: 155 g (62% of the theory), melting point: 158° to 159° C.

EXAMPLE 14

4-(4-n-Propylpiperazine-1-yl)-3-sulfamoylbenzoic acid

The reaction was carried out in a manner analogous to that of Example 1, using 150 ml of N-n-propylpiperazine instead of the N-methylpiperazine. The crystalline crude product was purified by boiling with a 2:1 mixture of ethanol and dimethylformamide, in which the final product was only difficultly soluble in the hot state.

Yield: 75 g (40% of the theory), degradation point: 305° C.

EXAMPLE 15

3-Dimethylsulfamoyl-4-(piperazine-1-yl)-benzoic acid

264 Grams of 4-chloro-3-dimethylsulfamoylbenzoic acid (1.0 mole) and 345 g of anhydrous piperazine were heated at 130° C, while stirring, for 1 hour. Subsequently the reaction mixture was dissolved in 2 l of water and the pH value was adjusted to 7 with 5N HCl. After having stood over night, the crystalline precipitate was suction-filtered, washed with water and tetrahydrofurane and recrystallized from water. Yield: 80 g (25% of the theory), degradation point: 330° C.

EXAMPLE 16

3-Dimethylsulfamoyl-4-(4-methylpiperazine-1-yl)-benzoic acid-amide 364 grams of 3-dimethylsulfamoyl-4-(4-methylpiperazine-1-yl)-benzoic acid-hydrochloride (1.0 mole) were heated for 1 hour under reflux with 1 l of thionylchloride. Subsequently the reaction mixture was evaporated, and the residue was triturated with 1 ml of petroleum ether. The 3-dimethylsulfamoyl-4-(4-methylpiperazine-1-yl)-benzoylchloride-hydrochloride which had separated in a crystalline form was suction-filtered, washed with petroleum ether and dried in vacuo.

Yield: 380 g (95% of the theory), degradation point: 223° C.

40 Grams of the acid chloride (0.1 mole) were introduced portionwise, at room temperature while stirring, into 0.4 l of 2N aqueous ammonia. A clear solution was obtained at first, from which the amide precipitated spontaneously in a crystalline state shortly after the chloride had been added. The substance, washed with water and dried on the steam bath, was analytically pure.

Yield: 19 g (55% of the theory), degradation point: 223° C.

EXAMPLE 17

3-Dimethylsulfamoyl-4-(4-methylpiperazine-1-yl)-benzoic acid-methylester

40 Grams of 3-dimethylsulfamoyl-4-(4-methylpiperazine-1-yl)-benzoylchloride-hydrochloride (0.1 mole) were heated for 2 hours under reflux in 1 l of methanol. Subsequently the methanol was distilled off and the residue was dissolved in 0.3 l of water. A small amount of undissolved amorphous material was removed by filtration and the pH value of the filtrate was adjusted to 8 by means of concentrated aqueous ammonia, whereupon the final product precipitated immediately in a crystalline state. After it had been washed with water, it was dried on the steam bath.

Yield: 28 g (82% of the theory), melting point: 179° to 181° C.

EXAMPLE 18

3-Dimethylsulfamoyl-4-(4-methylpiperazine-1-yl)-benzoic acid-benzylester-hydrochloride 40 Grams of 3-dimethylsulfamoyl-4-(4-methylpiperazine-1-yl)-benzoylchloride-hydrochloride (0.1 mole) were dissolved in 0.5 l of benzyl alcohol. 50 Milliliters of triethylamine were added dropwise to the solution, while stirring at room temperature. The mixture was then heated for 10 minutes on the steam bath and was subsequently evaporated in vacuo.

The evaporation residue crystallized when triturated with 0.3 l of water. The product suction-filtered, was washed with water and diethylether and then recrystallized from ethanol.

Yield: 35 g (77% of the theory), melting point: 202° C.

EXAMPLE 19

3-Dimethylsulfamoyl-4-(4-methylpiperazine-1-yl)-benzoic acid-diethylamide

40 Grams of 3-dimethylsulfamoyl-4-(4-methylpiperazine-1-yl)-benzoylchloride-hydrochloride (0.1 mole) were introduced portionwise, while stirring at room temperature, into a solution of 20 g of diethylamine in 0.4 l of tetrahydrofurane. After the addition had been completed, the mixture was stirred for another 30 minutes at room temperature, and subsequently the tetrahydrofurane was completely eliminated in vacuo. The evaporation residue crystallized when triturated with 0.2 l of water, and, after having been suction-filtered and dried, it was recrystallized from butylacetate.

Yield: 27 g (70% of the theory), melting point: 121° to 122° C.

EXAMPLE 20

4-(4-Ethylpiperazine-1-yl)-3-dimethylsulfamoyl-benzoic acid-hydrochloride

16 Grams of diethylsulfate were added dropwise, at room temperature, while being mixed in a vibro-mixer, to a solution of 31.5 g of 3-dimethylsulfamoyl-4-(piperazine-1-yl)-benzoic acid (0.1 mole), which had been prepared according to Example 15, in 0.3 l of 1N NaOH. The mixture was allowed to react for another 3 hours while being mixed in the vibro-mixer. Subsequently the solution was acidified with 5N HCl, and the separated hydrochloride was recrystallized from ethanol and water.

Yield: 32 g (85% of the theory), degradation point: 317° C.

EXAMPLE 21

3-Dibenzylsulfamoyl-4-(4-methylpiperazine-1-yl)-benzoic acid-hydrochloride

30 Grams of 4-(4-methylpiperazine-1-yl)-3-sulfamoylbenzoic acid (0.1 mole), which had been prepared according to Example 1, were dissolved in 0.5 l of 1N NaOH. Subsequently 35 g of benzylbromide were added dropwise, at room temperature, within 30 minutes, while the substance was mixed in a vibro-mixer. After the mixture had been reacted for another hour at room temperature, the precipitated by-products were separated by filtration.

When the reaction solution was adjusted to a pH value of 8 by means of 5N HCl, a resin precipitated. It was separated by decanting and was dissolved in 100 ml of ethanol. When 100 ml of ethanolic HCl of 10% strength were added to this solution, the final product crystallized in colorless prisms. After it had been allowed to stand for 1 hour at room temperature, it was suction-filtered, washed with ethanol and dried at 100° C.

Yield: 32.8 g (63% of the theory), melting point: 214° C.

EXAMPLE 22

4-(4-Methylpiperazine-1-yl)-3-sulfamoylbenzonitrile 43.5 Grams of 4-Chloro-3-Sulfamoylbenzonitrile (0.2 mole) were stirred with 45 g of N-methylpiperazine and 50 ml of dimethylformamide for 1 hour at a temperature of from 115° to 120° C, and the reaction solution was subsequently introduced into 0.5 l of water. The crystalline precipitate was suction-filtered, and the moist crude product which had been washed with water, was recrystallized from ethanol.

Yield: 34 g (61% of the theory), melting point: 207° C.

EXAMPLE 23

3-Dimethylsulfamoyl-4-(4-methylpiperazine-1-yl)-benzonitrile

In a manner analogous to that of Example 22, 49 g of 4-chloro-3-dmethylsulfamoylbenzonitrile (0.2 mole) were reacted with N-methylpiperazine, and the final product was recrystallized from ethanol.

Yield: 43 g (69% of the theory), melting point: 164° C.

EXAMPLE 24

4-(4-Benzylpiperazine-1-yl)-3-dimethylsulfamoylbenzoic acid-hydrobromide

The reaction mixture was prepared n a manner analogous to that of Example 20, however while using 20 g of benzylbromide instead of the diethylsulfate. After the reaction had been completed, the solution was filtered, and acidified with 2N HBr, and the hydrobromide which had been separated in a crystalline form was recrystallized from methanol.

Yield: 26 g (53% of the theory), degradation point: 262° to 263° C.

EXAMPLE 25

3-Dimethylsulfamoyl-4-(4-methylpiperazine-1-yl)-benzoic acid-n-butylester

40 Grams of 3-dimethylsulfamoyl-4-(4-methylpiperazine-1-yl)-benzoylchloride-hydrochloride (0.1 mole) were heated under reflux for 2 hours with 0.4 l of n-butanol. Subsequently the n-butanol was eliminated in vacuo, the residue was dissolved in 0.5 l of water, and the pH value of the filtered solution was adjusted to 8.5 by means of 2N ammonia. The crystalline precipitate was suction-filtered, washed with water, then dried in vacuo at 40° C and finally dissolved and reprecipitated from a mixture of acetic ester and diisopropylether.

Yield: 22 g (57% of the theory), melting point: 118° to 119° C.

EXAMPLE 26

3-Dimethylsulfamoyl-4-(4-methylpiperazine-1-yl)-benzoic acid-N-methylanilide

A solution of 35 g of N-methylaniline in 0.3 l of tetrahydrofurane was mixed with 40 g of 3-dimethylsulfamoyl-4-(4-methylpiperazine-1yl)-benzoylchloride-hydrochloride, and the mixture was heated under reflux for 1 hour. After the tetrahydrofurane had been eliminated in vacuo, the residue was treated with 0.5 l of 1N HCl, and a small amount of brown resin was filtered off. After the pH value of the filtrate had been adjusted with NaOH, a resin was separated which crystallized after having been allowed to stand over night at room temperature. The air-dried crude product was purified by being recrystallized from an approximately 3:1 mixture of acetic ester and methanol.

Yield: 22 g (50% of the theory), melting point: 182° C.

EXAMPLE 27

3-Dimethylsulfamoyl-4-(4-methylpiperazine-1-yl)-benzoic acid-dibenzylamide

40 Grams of 3-dimethylsulfamoyl-4-(4-methylpiperazine-1-yl)-benzoylchloride-hydrochloride (0.1 mole) were added portionwise at room temperature, while stirring, to a solution of 22 g of dibenzylamine and 20 g of triethylamine in 0.2 l of tetrahydrofurane. Subsequently the reaction mixture was heated for another hour under reflux, and then the tetrahydrofurane was eliminated in vacuo. The amorphous residue was dispersed in 0.5 l of acetic ester and 0.5 l of 1N NaOH. The acetic ester phase was separated and was dried over magnesium sulfate. The acetic ester solution was then concentrated to half its volume and was mixed with the same volume of petroleum ether under heat. Upon trituration the final product crystallized and was suction-filtered after having been cooled with ice water for 1 hour.

Yield: 19 g (37% of the theory), melting point: b 157° C.

EXAMPLE 28

3-Dimethylsulfamoyl-4-(4-methylpiperazine-1-yl)-benzoic acid-4-phenylpiperazide

The reaction mixture was prepared in a manner analogous to that of Example 27, however while using 20 g of N-phenylpiperazine instead of the dibenzylamine. The acetic ester solution of the reaction product was completely evaporated, and the residue was recrystallized from methanol.

Yield: 23 g (48% of the theory), melting point: 192° C.

EXAMPLE 29:

3-Dimethylsulfamoyl-4-(4-methylpiperazine-1-yl)-benzoic acid-isobutylamide

40 Grams of 3-dimethylsulfamoyl-4-(4-methylpiperazine-1-yl)-benzoylchloride-hydrochloride (0.1 mole) were introduced portionwise, while stirring, into a solution of 30 g of isobutylamine in 0.4 l of tetrahydrofurane. The mixture, whose temperature rose to about 50° C, was subsequently heated for another 10 minutes under reflux and was then concentrated to half its volume.

After 0.5 l of acetic ester had been added, the mixture was shaken twice with 0.2 l portions of 1N NAOH. Subsequently the organic phase was separated, evaporated completely, and the residue was recrystallized from acetic ester.

Yield: 20 g (52% of the theory), melting point: 159° to 160° C.

EXAMPLE 30

6-Chloro-4-(4-methylpiperazine-1-yl)-3-sulfamoylbenzoic acid

A mixture of 50 g of 4,6-dichloro-3-sulfamoylbenzonitrile, 0.1 l of dioxane and 21 g of N-methylpiperazine was stirred for 2 hours at 100° C. Subsequently, the reaction solution was introduced into 0.3 l of water, the crystalline precipitate was suction-filtered, washed with water and recrystallized from ethanol.

Yield: 33 g (52% of the theory), melting point: 226° to 288° C.

EXAMPLE 31

3-Diethylsulfamoyl-4-(4-methylpiperazine-1-yl)-benzoic acid

29 Grams of 4-chloro-3-diethylsulfamoyl-benzoic acid were heated with 30 g of N-methylpiperazine for 4 hours at 140° C. Subsequently the reaction solution, which had cooled down to 80° C, was introduced into 0.4 l of water, and the solution was neutralized with 5N HCl. As soon as the precipitate which was amorphous at first, became crystallized, it was suction-filtered and recrystallized from methanol.

Yield: 25 g (70% of the theory), melting point: 211° C.

EXAMPLE 32

3-Allylsulfamoyl-4-(4-methylpiperazine-1-yl)-benzoic acid-hydrochloride

A mixture of 28 g of 3-allylsulfamoyl-4-chlorobenzoic acid, 30 g of N-methylpiperazine and 20 ml of dimethylformamide was heated for 4 hours at 140° C. When the reaction solution was subsequently introduced into 0.3 l of 2N HCl, the monohydrochloride crystallized immediately. The product was then purified by recrystallization from water.

Yield: 29 g (77% of the theory), degradation point: 276° C.

EXAMPLE 33

4-(4-Methylpiperazine-1-yl)-3-tetrahydrofurfurylsulfamoylbenzoic acid

The reaction was carried out in a manner analogous to that of Example 31, using 32 g of 4-chloro-3-tetrahydrofurfurylsulfamoyl-benzoic acid and 30 g of N-methylpiperazine. The crude product was purified by recrystallization from ethanol.

Yield: 24 g (64% of the theory), melting point: 204° C.

EXAMPLE 34

3-(N-methylcyclohexylaminosulfonyl)-4-(4-methylpiperazine-1-yl)-benzoic acid

The reaction was carried out in a manner analogous to that of Example 31, using 33 g of 4-chloro-3-(N-methylcyclohexylaminosulfonyl)-benzoic acid and 30 g of N-methylpiperazine. The moist crude product, which had been washed with water, was freed from by-products by boiling with methanol.

Yield: 31 g (78% of the theory), melting point: 208° C.

EXAMPLE 35

3-(2-Ethoxyethylsulfamoyl)-4-(4methylpiperazine-1-yl)-benzoic acid-dihydrochloride 31 Grams of 3-(2-ethoxyethylsulfamoyl)-4-chlorobenzoic acid and 30 g of N-methylpiperazine were heated for 4 hours at 140° C. Subsequently the excess base was eliminated in vacuo. The residue was dissolved in 0.2 1 l of water, and the solution was adjusted to a pH value of 9.5 by means of 2N NaOH. After evaporating the solution in vacuo, the residue was extracted with boiling ethanol, and the solution, which had been concentrated to 100 ml, was mixed with 100 ml of ethanolic HCl of 10% strength. After having been triturated and cooled, the final product crystallized within a short time and was dried at 60° C after washing with ethanol.

Yield: 23 g (52% of the theory), degradation point: 266° C.

EXAMPLE 36

4-(4-Methylpiperazine-1-yl)-3-n-propylsulfamoylbenzoic acid-hydrochloride 37.6 Grams of 3-allylsulfamoyl-4-(4-methylpiperazine-1-yl)-benzoic acid-hydrochloride (0.1 mole), prepared according to Example 32, were dissolved in 0.3 l of tetrahydrofurane and were hydrogenated in the presence of palladium black at 30° C and at 40 atmospheres until no more hydrogen was absorbed. Subsequently the catalyst was separated, the solution was evaporated, and the residue was recrystallized from water.

Yield: 33.2 g (88% of the theory), degradation point: 268° C.

EXAMPLE 37

4-(4-Methylpiperazine-1-yl)-3-pyrrolidinosulfonylbenzoic acid-hydrochloride 29.0 Grams of 4-chloro-3-pyrrolidinosulfonylbenzoic acid (0.1 mole) were heated with 50 ml of N-methylpiperazine for 4 hours under reflux. Subsequently the reaction solution was introduced into 0.3 l of water, and the pH value of the mixture was adjusted to 3.0 by means of 5N HCl. After having been allowed to stand over night at room temperature, the precipitate was suction-filtered, recrystallized from water and dried at 100° C.

Yield: 19.0 g (49% of the theory), degradation point: 306° to 307° C.

EXAMPLE 38

4-(4-Methylpiperazine-1-yl)-3-piperidinosulfonylbenzoic acid-hydrochloride

The reaction was carried out in a manner analogous to that of Example 37, using 30.4 g of 4-chloro-3-piperidinosulfonyl benzoic acid (0.1 mole) and 50 ml of N-methylpiperazine.

Yield: 22.5 g (56% of the theory), degradation point: 259° to 260° C.

EXAMPLE 39

4-(4-Methylpiperazine-1-yl)-3-sulfamoylbenzoic acid-N-methylbenzylamide 33.8 Grams of 4-chloro-3-sulfamoylbenzoic acid-N-methylbenzylamide (0.1 mole) were heated with 80 ml of N-methylpiperazine for 4 hours under reflux. Subsequently the solution was introduced into 0.4 l of water, the pH value of the mixture was adjusted to 9.0 by means of glacial acetic acid, and the mixture was then allowed to stand for 2 days at room temperature. The crystalline precipitate was separated and was recrystallized from a mixture of ethanol and water.

Yield: 29.7 g (74% of the theory), melting point: 132° C.

EXAMPLE 40

4-(4-Methylpiperazine-1-yl)-3-sulfamoylbenzoic acid-benzylamide-hydrochloride

The reaction was carried out in a manner analogous to that of Example 39, using 32.5 g of 4-chloro-3-sulfamoylbenzoic acid-benzylamide (0.1 mole) and 80 ml of N-methylpiperazine. The base, which had separated in an amorphous form, was dissolved in 0.2 l of ethanol. After 0.1 l of ethanolic HCl of 20% strength had been added, the hydrochloride crystallized.

Yield: 31.5 g (74% of the theory), melting point: 155° C with evolution of gas.

We claim:

1. A basically-substituted 3-morpholinosulfonyl benzoic acid of the formula

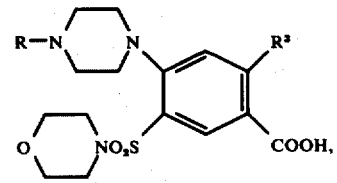

salts thereof with physiologically tolerable acids, and salts thereof with physiologically tolerable bases, wherein R is hydrogen, alkyl having 1 to 6 carbon atoms, or benzyl, and $R^3$ is hydrogen, halogen, or alkyl having 1 to 4 carbon atoms.

2. The compound defined in claim 1 which is 4-(4-methylpiperazine-1-yl)-3-morpholinosulfonylbenzoic acid.

3. A pharmaceutical composition for the treatment of high blood pressure which consists essentially of an effective amount of a compound as in claim 1 in admixture with a pharmaceutical carrier.

4. A method for treating high blood pressure in a patient suffering therefrom which comprises administering an effective amount of a compound as in claim 1.

* * * * *